(12) United States Patent
Gerard et al.

(10) Patent No.: US 9,427,211 B2
(45) Date of Patent: Aug. 30, 2016

(54) ULTRASOUND IMAGING SYSTEM AND METHOD

(75) Inventors: Olivier Gerard, Horten (NO); Jan Otto Strand, Horten (NO); Andreas M. Ziegler, Oslo (NO)

(73) Assignee: General Electric Company, Schenectady, NY (US)

( * ) Notice: Subject to any disclaimer, the term of this patent is extended or adjusted under 35 U.S.C. 154(b) by 521 days.

(21) Appl. No.: 13/545,332

(22) Filed: Jul. 10, 2012

(65) Prior Publication Data
US 2014/0013849 A1 Jan. 16, 2014

(51) Int. Cl.
| | | |
|---|---|---|
| *G01N 29/00* | (2006.01) | |
| *A61B 8/00* | (2006.01) | |
| *G01N 29/06* | (2006.01) | |
| *G01N 29/44* | (2006.01) | |
| *G01S 7/52* | (2006.01) | |
| *A61B 8/08* | (2006.01) | |
| *G01S 15/89* | (2006.01) | |

(52) U.S. Cl.
CPC .............. *A61B 8/463* (2013.01); *A61B 8/483* (2013.01); *G01N 29/0609* (2013.01); *G01N 29/0645* (2013.01); *G01N 29/44* (2013.01); *G01S 7/52063* (2013.01); *G01S 7/52073* (2013.01); *G01S 7/52074* (2013.01); *G01S 7/52084* (2013.01); *G01S 15/8993* (2013.01); *A61B 8/469* (2013.01); *G01N 2291/02475* (2013.01); *G01S 7/5208* (2013.01); *G01S 15/8925* (2013.01)

(58) Field of Classification Search
None
See application file for complete search history.

(56) References Cited

U.S. PATENT DOCUMENTS

| | | | |
|---|---|---|---|
| 6,245,017 B1 | 6/2001 | Hashimoto et al. | |
| 6,276,211 B1 | 8/2001 | Smith | |
| 6,443,896 B1 | 9/2002 | Detmer | |
| 2003/0097067 A1* | 5/2003 | Poland et al. | 600/443 |
| 2003/0195421 A1* | 10/2003 | Demers et al. | 600/437 |
| 2005/0001982 A1* | 1/2005 | Youn | 352/86 |
| 2005/0281444 A1* | 12/2005 | Lundberg et al. | 382/128 |
| 2005/0283078 A1* | 12/2005 | Steen | A61B 8/06 600/447 |
| 2007/0255139 A1* | 11/2007 | Deschinger et al. | 600/443 |
| 2010/0067761 A1* | 3/2010 | Jakobsson et al. | 382/131 |
| 2011/0125003 A1* | 5/2011 | Reach | A61F 2/4657 600/407 |

* cited by examiner

*Primary Examiner* — Hezron E Williams
*Assistant Examiner* — Tarun Sinha (57) ABSTRACT

An ultrasound imaging system and method includes acquiring data including a first plane and a second plane. The system and method includes adjusting a first orientation of the first plane and automatically adjusting a second orientation of the second plane in order to maintain a fixed relationship between the second plane and the first plane.

20 Claims, 7 Drawing Sheets

FIG. 5

ULTRASOUND IMAGING SYSTEM AND METHOD

FIELD OF THE INVENTION

This disclosure relates generally to an ultrasound imaging system and method for adjusting a first plane and automatically adjusting a second plane in order to maintain a fixed relationship between the first plane and the second plane.

BACKGROUND OF THE INVENTION

In order to obtain ultrasound images of two or more planes with high temporal resolution, conventional ultrasound systems may utilize a multi-plane probe, such as a bi-plane probe or a tri-plane probe. The multi-plane probe typically has two or more transducer arrays disposed at different angles with respect to each other. The multi-plane probe usefully provides images of two or more planes that may be acquired and viewed in real-time. However, an ultrasound imaging system with a conventional multi-plane probe does not allow the user to control the angle of rotation between each of the planes acquired by the transducer arrays.

A conventional ultrasound system including a 2D matrix array has the capability to fully steer beams in both azimuth and elevation directions. Conventional 2D matrix arrays may be used to acquire volumetric datasets or to acquire data for two or more planes disposed at an angle with respect to each other, in a manner like a bi-plane probe. Advantageously, since a 2D matrix array probe is fully steerable in both elevation and azimuth, it may be used to acquire and display images of two or more planes disposed at arbitrary angles with respect to each other in real-time. However, conventional systems typically require the user to individually adjust the orientation of each plane separately. This is burdensome for the operator during situations where the operator would like to keep a fixed relationship between the multiple planes and the images of the planes.

For these and other reasons an improved method and ultrasound imaging system for adjusting the orientations of multiple planes is required.

BRIEF DESCRIPTION OF THE INVENTION

The above-mentioned shortcomings, disadvantages and problems are addressed herein which will be understood by reading and understanding the following specification.

In an embodiment, a method of ultrasound imaging includes acquiring multi-plane data including a first plane and a second plane, wherein the second plane is in a fixed relationship with respect to the first plane. The method includes displaying a first image of the first plane and a second image of the second plane. The method includes adjusting a first orientation of the first plane with a user interface and automatically adjusting a second orientation of the second plane to maintain the fixed relationship between the second plane and the first plane. The method includes displaying a first updated image of the first plane and a second updated image of the second plane, wherein the first updated image shows the first plane after adjusting the first orientation and the second updated image shows the second plane after automatically adjusting the second orientation.

In an embodiment, an ultrasound imaging system includes a probe, a display device, a user interface, and a processor in electronic communication with the probe, the display device, and the user interface. The processor is configured to control the probe to acquire multi-plane data including a first plane and a second plane and display a first image of the first plane and a second image of the second plane on the display device while acquiring the multi-plane data. The processor is configured to enable a user to adjust a first orientation of the first plane with the user interface while acquiring the multi-plane data, and automatically adjust a second orientation of the second plane so that the first plane and the second plane are maintained in a fixed relationship relative to each other.

In another embodiment, an ultrasound imaging system includes a probe, a display device, a user interface, and a processor in electronic communication with the probe, the display device, and the user interface. The processor is configured to control the probe to acquire data of a first plane and a second plane. The processor is configured to display a first image of the first plane and a second image based on the data. The processor is configured to adjust a first orientation of the first plane and a second orientation of the second plane in lock-step in response to a control input through the user interface adjusting only one of the first orientation of the first plane and the second orientation of the second plane.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
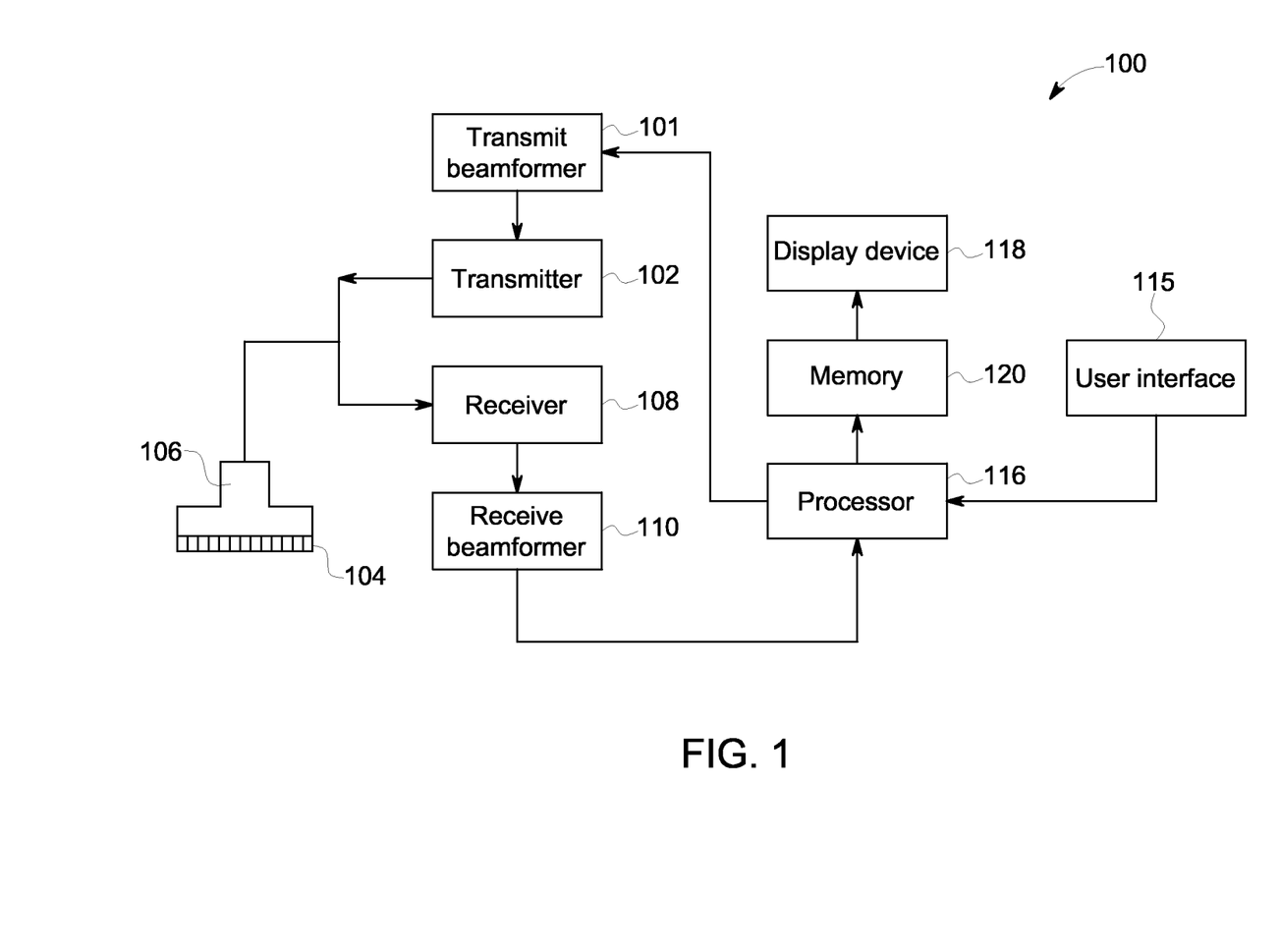
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within a probe 106 to emit pulsed ultrasonic signals into a body (not shown). According to an embodiment, the probe 106 may be a 2D matrix array probe. Still referring to FIG. 1, the pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit and/or the receive beamforming. For example, all or part of the transmit beamformer 101, the transmitter 102, the receiver 108 and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. A user interface 115 may be used to control operation of the ultrasound imaging system 100, including, to control the input of patient data, to change a scanning or display parameter, and the like. The user interface 115 may include one or more of the following: a rotary, a mouse, a keyboard, a trackball, hard keys linked to specific actions, soft keys that may be configured to control different functions, and a graphical user interface displayed on the display device.

The ultrasound imaging system 100 also includes a processor 116 to control the transmit beamformer 101, the transmitter 102, the receiver 108 and the receive beamformer 110. The processor 116 is in electronic communication with the probe 106. For purposes of this disclosure, the term "electronic communication" may be defined to include both wired and wireless connections. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. The processor 116 may include a central processor (CPU) according to an embodiment. According to other embodiments, the processor 116 may include other electronic components capable of carrying out processing functions, such as a digital signal processor, a field-programmable gate array (FPGA) or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation can be carried out earlier in the processing chain. The processor 116 is adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire images at a real-time rate of 7-20 volumes/sec. The ultrasound imaging system 100 may acquire 2D data of one or more planes at a significantly faster rate. However, it should be understood that the real-time volume-rate may be dependent on the length of time that it takes to acquire each volume of data for display. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, 10 Hz to 30 Hz. Images generated from the data may be refreshed at a similar frame-rate. Other embodiments may acquire and display data at different rates. For example, some embodiments may acquire data at a volume-rate of less than 10 Hz or greater than 30 Hz depending on the size of the volume and the intended application. A memory 120 is included for storing processed volumes of acquired data. In an exemplary embodiment, the memory 120 is of sufficient capacity to store at least several seconds worth of volumes of ultrasound data. The volumes of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in an image memory, from which the images are read and displayed.

Figure 2:
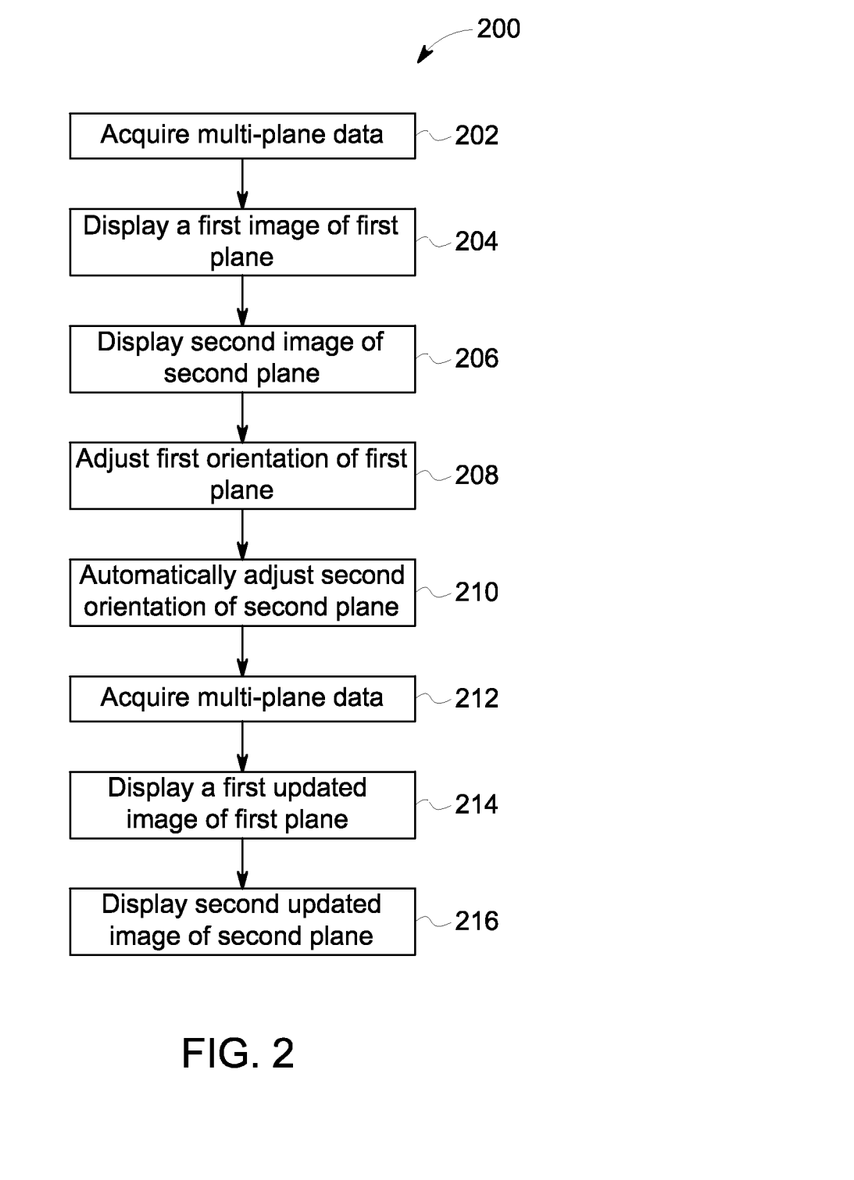
FIG. 2 is a flow chart of a method in accordance with an embodiment.

FIG. 2 is flow chart of a method in accordance with an embodiment. The individual blocks of the flow chart represent steps that may be performed in accordance with the method 200. Additional embodiments may perform the steps shown in a different sequence and/or additional embodiments may include additional steps not shown in FIG. 2. The technical effect of the method 200 is the automatic adjustment of an orientation of a second plane in response to the adjustment of an orientation of a first plane with a user interface.

Referring to FIG. 1 and FIG. 2, the method 200 will be described according to an exemplary embodiment using the ultrasound imaging system 100. It should be appreciated by those skilled in the art that the method 200 may be implemented by other ultrasound imaging system in accordance with other embodiments.

At step 202, the processor 116 controls the probe 106 to acquire multi-plane data. The processor 116 may control the transmit beamformer 101, the transmitter 102, the receiver 108, and the receive beamformer 110 in the process of controlling the probe 106 in order to acquire the multi-plane data of the desired planes. For purposes of this disclosure, the term "multi-plane data" is defined to include ultrasound data of two or more distinct planes. Each of the planes represented in the multi-plane data is disposed at a different orientation than the other planes in the multi-plane data. For purposes of this disclosure, the term "orientation" is defined to include the geometric position of a plane with respect to a transducer array of a probe. According to an embodiment, the probe 106 may be a 2D matrix array probe that is fully steerable in both an elevation and an azimuth direction. Using a 2D matrix array probe allows the processor 116 to acquire multi-plane data representing planes disposed at any arbitrary orientation within the field-of-view of the 2D matrix array probe. The user may be able to select the orientations of the planes represented in multi-plane ultrasound data or the method 200 may acquire multi-plane data of two or more planes at preset orientations. According to an exemplary embodiment, the method 200 will be hereinafter described according to an embodiment where the multi-plane data comprises data of two planes.

Figure 3A:
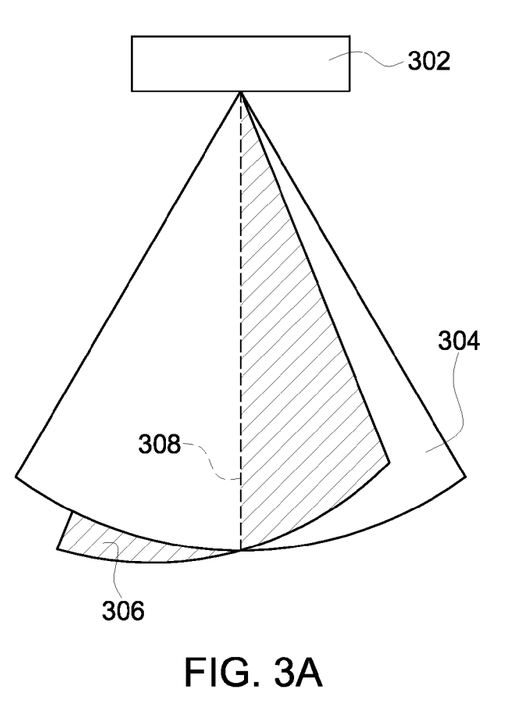
FIG. 3A is a schematic diagram of two planes in accordance with an exemplary embodiment.

Referring to FIG. 3A, a schematic diagram of two planes is shown in accordance with an exemplary embodiment. FIG. 3A includes a transducer array 302, a first plane 304, and a second plane 306. The first plane 304 and the second plane 306 are shown in a perspective view in order to more clearly demonstrate the relative orientation of the first plane 304 with respect to the second plane 306 and the transducer array 302. A normal line 308 is also shown on FIG. 3A. The normal line 308 is perpendicular to the center of the transducer array 302. According to an embodiment shown in FIG. 3A, the first plane 304 and the second plane 306 intersect along the normal line 308. It should be appreciated that according to other embodiments that will be described hereinbelow, the first plane 304 and the second plane 306 may be adjusted into positions and/or orientations other than those shown in FIG. 3A.

Figure 3B:
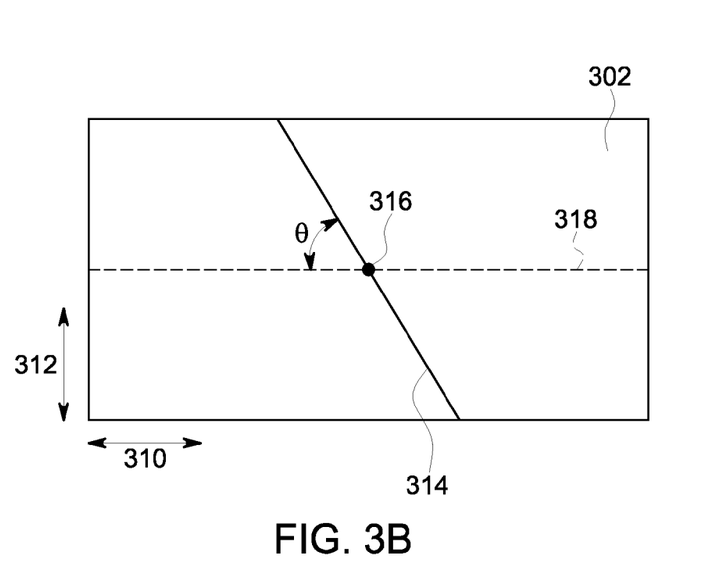
FIG. 3B is a schematic diagram showing a rotation of a plane with respect to a transducer array in accordance with an exemplary embodiment.

FIG. 3B is a schematic diagram illustrating a rotation of a plane 316 with respect to the transducer array 302. The transducer array 302 shown in FIG. 3B is the same as the transducer array shown in FIG. 3A. The plane 316 is distinct from planes 304 and 306 shown in FIG. 3A. The transducer array 302 includes a plurality of transducer elements (not shown) arranged in a 2D array. The transducer array 302 includes an azimuth direction 310 and an elevation direction 312. According to an exemplary embodiment, a rotation θ of plane 314 is measured in degrees from a line parallel to the azimuth direction 310. A dashed line 318 represents an example of a line that is parallel to the azimuth direction 310. The example shown in FIG. 3B shows the plane 314 passing through a center point 316 of the transducer array 302, but it should be understood that not all planes need to pass through the center point 316.

Figure 3C:
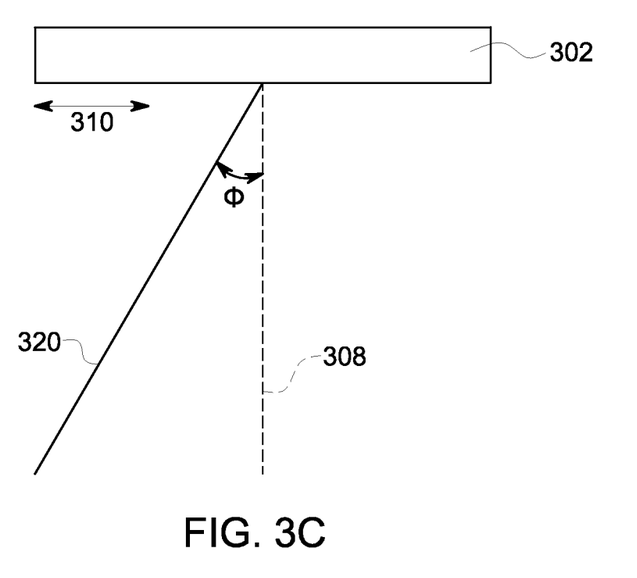
FIG. 3C is a schematic diagram showing a tilt of a plane with respect to a transducer array.

FIG. 3C is a schematic diagram illustrating a tilt of a plane 320 with respect to the transducer array 302. The transducer array 302 is the same as the transducer array shown in FIGS. 3A and 3B. The azimuth direction 310 is shown in relation to the transducer array 302. The plane 320 is distinct from planes 304 and 306 shown in FIG. 3A and from plane 314 shown in FIG. 3B. A tilt Φ of the plane 320 is measured in degrees from the normal line 308 according to an exemplary embodiment.

Referring to FIGS. 1, 2 and 3, at step 204, the processor 116 displays a first image of the first plane 304 on the display device 118. Next, at step 206, the processor 116 displays a second image of the second plane 306 on the display device 118. According to an embodiment, the first image and the second image may be shown at substantially the same time on the display device 118. For example, the processor 116 may display the first image in a first portion of a screen of the display device 118 and the second image in a second portion of the screen of the display device 118. According to other embodiments where the display device 118 includes multiple screens or monitors, the first image and the second image may be shown on separate monitors at substantially the same time. According to an embodiment, the processor 116 may continue to acquire the multi-plane data at step 202 during the display of the first image of the first plane 304 and the second image of the second plane 306. For example, the processor 116 may repeatedly acquire multi-plane data of the first plane 304 and the second plane 306. As each additional image or frame of the first plane 304 or the second plane 306 is acquired, the processor 116 updates the display of the first image or second image respectively on the display device 118. In this way, live or real-time images of the first plane 304 and the second plane 306 may be displayed on the display device 118. The display of live or real-time images of planes is well-known by those skilled in the art and, as such, will not be described in additional detail.

At step 208, a user adjusts a first orientation of the first plane 304. The first orientation of the first plane 304 may be defined with respect to the transducer array 302. According to an exemplary embodiment, the first orientation of the first plane 304 may be described in terms of degrees of rotation from a predefined axis of the probe and in terms of degrees of tilt as shown in FIGS. 3B and 3C. It should be appreciated that the orientation of the first plane 304 may be defined in a different manner according to additional embodiments. Additional description about exemplary ways to adjust the orientation will be described hereinafter.

At step 210, the processor 116 automatically adjusts a second orientation of the second plane 306 in order to maintain a fixed relationship between the first plane 304 and the second plane 306.

Figure 4A:
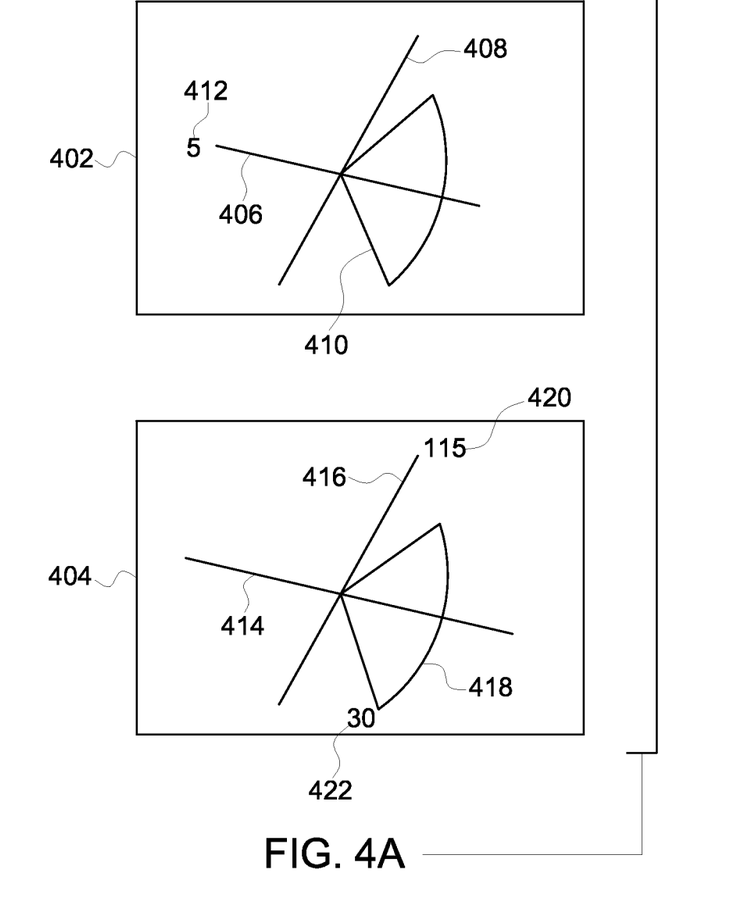
FIG. 4A is a schematic representations of a graphical user interface in accordance with an embodiment.
Figure 4B:
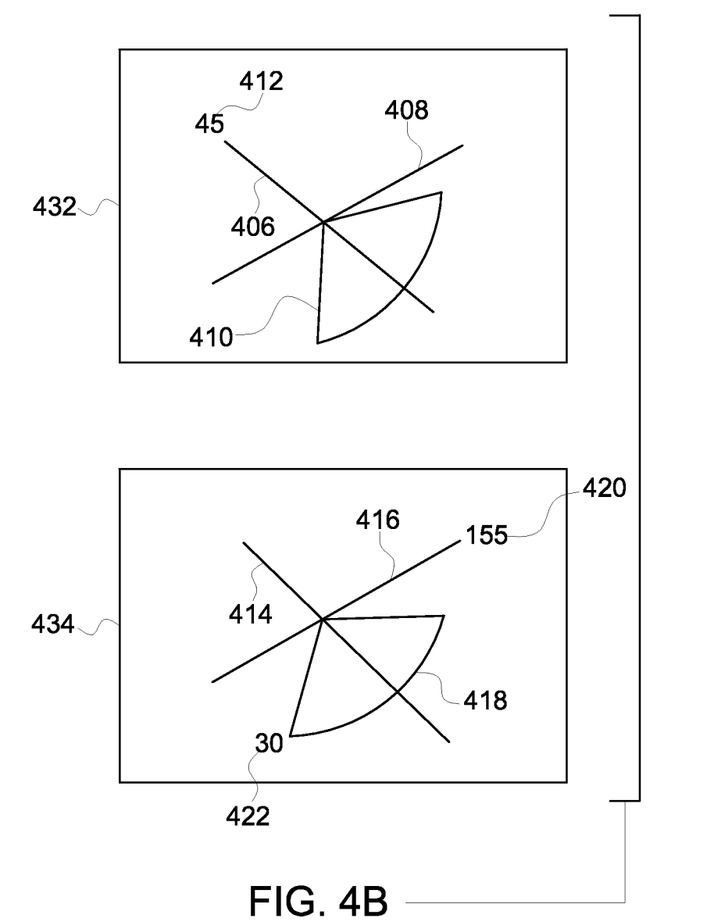
FIG. 4B is a schematic representations of a graphical user interface in accordance with an embodiment.

Referring to FIGS. 4A and 4B, schematic representations of a graphical user interface is shown in accordance with an embodiment. The graphical user interface of FIGS. 4A and 4B will be used to describe a particular embodiment as well as to demonstrate an exemplary workflow.

FIG. 4A includes a first icon 402 and a second icon 404. The first icon 402 represents the orientation of the first plane 304. The first icon 402 includes a first line 406, a second line 408, a tilt icon 410, and a rotation value 412. The first line 406 represents the first plane 304 and the second line 408 represents the second plane 306. According to an embodiment, the first line 406 may be bolded to further indicate the plane associated with the first icon 402. The rotation value 412 is 5 degrees, which means that the first plane 304 is rotated 5 degrees from a line parallel to an azimuth direction on the transducer array 302. The rotation value 412 may indicate the rotation with respect to a different reference line or direction according to other embodiments. There is no value associated with the tilt icon 410, which means that the first plane 304 is not tilted with respect to the normal line 308.

The second icon 404 represents the orientation of the second plane 306. The second icon 404 includes a first line 414, a second line 416, a tilt icon 418, and a rotation value 420. The first line 414 represents the first plane 304 and the second line 416 represents the second plane 306. According to an embodiment, the second line 416 may be bolded to further indicate the plane associated with the second icon 404. The rotation value 420 is 115 degrees, which means that the second plane 306 is rotated 115 degrees from a line parallel to an azimuth direction on the transducer array 302. The second icon 404 also includes a tilt value 422, which is 30 degree according to the embodiment of FIG. 4A. The tilt value 422 represents the tilt or inclination of the second plane 306. According to an embodiment, both the first and second planes may originate from the same point in the transducer array 304. The tilt may be determined by pivoting the plane in a direction perpendicular to the plane while keeping a point of origin for acquisition fixed on the transducer array 304.

According to an embodiment, at step 202 the multi-plane data may be initially acquired from the planes represented by the first icon 402 and the second icon 404 shown in FIG. 4A. The first icon 402 and the second icon 404 of FIG. 4A represent the positions of the planes with respect to the transducer array 302 and, in addition, they also define a fixed relationship between the second plane 306 and the first plane 304. For purposes of this disclosure, a plane may be described by rotation and tilt. As discussed previously, the first plane is described by a rotation of 5 degrees and a tilt of 0 degrees, while the second plane is described by a rotation of 115 degrees and a tilt of 30 degrees.

FIG. 4B includes a first icon 432 and a second icon 434. The first icon 432 includes the same elements as the first icon 402 of FIG. 4A, and, therefore, identical reference numbers have been used. The second icon 434, shown in FIG. 4B, includes the same elements as the second icon 404 of FIG. 4A and identical reference numbers have also been used. In the first icon 432, the rotation value 412 of the first plane 304 is 45 degrees while the tilt value remains 0 degrees. In the second icon 434, the rotation value 420 of the second plane is 155 degrees while the tilt remains 30 degrees. Therefore, comparing the change from FIG. 4A to FIG. 4B, the first plane 304 and the second plane 306 have both been rotated clockwise by 40 degrees. However, the tilts of the first plane 304 and the second plane 306 were not changed according to the exemplary embodiment shown in FIGS. 4A and 4B.

Referring back to the method 200, at step 208, the user adjusts the first orientation of the first plane 304. According to an embodiment, the user may use a rotatory or a track ball to control the orientation of the first plane 304. According to other embodiments, the user may use a graphical user interface, such as the icons shown in FIG. 4A, to control the orientation of the first plane 304. For example, the user may adjust the rotation by repositioning the selected line with a mouse or a trackball. According to the embodiment shown in FIGS. 4A and 4B, the user may adjust the plane 304 from an angle of 5 degrees as shown in the first icon 402 to an angle of 45 degrees as shown in the first icon 432. According to the exemplary embodiment, the tilt of the first plane and the second plane is not changed. However, it should be appreciated that according to other embodiments, the user may also adjust the tilt of the first or second plane at step 208. Additionally, the user may translate either the first plane or the second plane to a different location while keeping the relative orientation constant with respect to the transducer array 302.

FIG. 4A schematically represents a fixed relationship between the first plane and the second plane as defined by rotation and translation. At step 210, the processor 116 automatically adjusts the second orientation of the second plane in order to maintain the fixed relationship between the second plane 306 and the first plane 304. So, according to the exemplary embodiment, as the user adjusts the rotation of the first plane 304 from 5 to 45 degrees, the processor 116 automatically adjusts the second orientation of the second plane 306 by adjusting the rotation from 115 to 155 degrees at step 210. Therefore, even though both the first plane 304 and the second plane 306 have been rotated clockwise by 40 degrees with respect to the transducer array 302, the second plane 306 and the first plane 304 maintain the same fixed relationship.

According to other embodiments, the user may also adjust the tilt of the first plane as part of step 208. According to an embodiment, the user may select the plane to adjust and then adjust the tilt of that plane with a user interface including a rotary, a trackball, a mouse, or a graphical user interface. For example, the user may select the plane, and then implement the rotary or trackball to adjust the tilt of the selected plane. Additionally, the user may select the plane through a graphical user interface, such as the tilt icon 410, and adjust the tilt by dragging a corner of the tilt icon 410. According to an embodiment where the user adjusts a tilt of the first plane 304 at step 208, the processor 116 would automatically adjust the second orientation of the second plane 306 by applying the same tilt in order to maintain the fixed relationship between the first plane 304 and the second plane 306 at step 210. The processor 116 adjusts the orientations of the first plane 304 and the second plane 306 in lock-step. That is, the processor applies the same changes in orientation to both the first plane 304 and the second plane 306 in order to keep the first plane 304 in a fixed position with respect to the second plane 306 while the user applies a control input through the user interface 115. By adjusting both of the planes in lock-step, the user is able to adjust the positions of multiple planes with only a single set of control inputs. When the orientations of two or more planes are adjusted in lock-step, the orientations of the planes are adjusted as if the two planes were a single entity. This allows the user to maintain the relative positioning of the planes with respect to each other during the adjustment process.

Next, at step 212, the processor controls the acquisition of additional multi-plane data. The additional multi-plane data includes the first plane 304 after the user has adjusted the first orientation of the first plane 304 and the second plane 306 after the processor 116 has automatically adjusted the second orientation of the second plane 306.

At step 214, a first updated image of the first plane 304 is displayed on the display device in place of the first image. The first updated image represents the first plane 304 after the first orientation of the first plane 304 has been adjusted at step 208. Then, at step 216, a second updated image of the second plane 306 is displayed in place of the second image. The second updated image represents the second image after the second orientation of the second plane has been automatically adjusted at step 210.

According to an exemplary embodiment, the processor 116 may control the probe 106 to repeatedly acquire multi-plane data during all of the method 200. The processor 116 may also display images in real-time as the multi-plane data is acquired. That is, multi-plane data is acquired and images of the first plane 304 and the second plane 306 are displayed as soon as additional frames of the planes are acquired. According to this embodiment, the user may adjust a first orientation of the first plane 304 at step 208, and at step 210 the processor 116 will automatically adjust the second orientation of the second plane 306 to maintain the fixed relationship of the planes with respect to each other. The changes in orientation of the first plane 304 and the second plane 306 will then be reflected in updated images that are displayed in real-time as additional multi-plane data is acquired. According to other embodiments, the user may adjust the orientation of the second plane 306 and the processor 116 may automatically adjust the orientation of the first plane 304 to maintain the fixed relationship between the two planes.

According to another embodiment, the method 200 shown in FIG. 2 may be modified so that volumetric data, such as 3D or 4D data, is acquired instead of multi-plane at step 202. The user may then view two or more slices or planes from the volumetric data. According to an embodiment, the two or more planes generated from the volumetric data may be adjusted in lock-step, so that the relative orientations of the planes are maintained while the orientation of the planes is adjusted. For example, the processor 116 may generate a first image of a first plane at a first orientation and a second image of a second plane at a second orientation that is different from the first plane's orientation. Then, the user may apply adjustments to the orientation of either the first plane or the second plane. The processor 116 may then automatically apply the same orientation adjustments to the other of the first plane and the second plane to maintain a fixed relationship between the first plane and the second plane during the process of adjusting the orientation. If may be desirable to adjust the orientation of either plane independently, so the processor 116 may be configured to allow independent adjustment of either the first plane or the second plane as well. Additionally, since the images are generated from the volumetric data, the position of the planes may also be adjusted by translating the planes. According to an embodiment, the fixed relationship between the first plane and the second plane may be maintained during translational adjustments as well. According to an embodiment, the process of rotating two or more planes in lock-step that were generated from volumetric data may be used during a pre-mode to identify bi-plane planes or slices. For example, the volumetric data may be used to identify the most appropriate planes and then multi-plane data may be acquired for those planes, potentially resulting in data with improvements in frame-rate, resolution or field-of-view.

Figure 5:
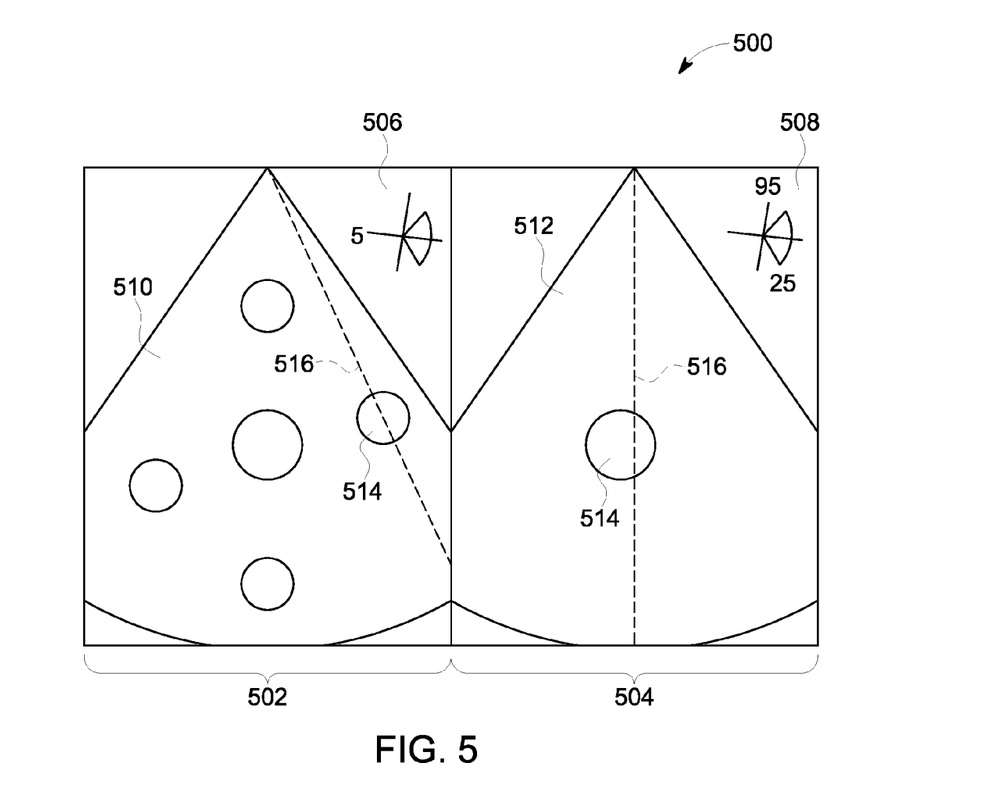
FIG. 5 is a schematic representation of a screen shot in accordance with an embodiment.

FIG. 5 is a schematic representation of a screen shot which may be used to display a first image of a first plane and a second image of a second plane in accordance with an embodiment. The screen shot 500 includes a first portion 502 and a second portion 504. The first portion 502 includes first image 510 of a first plane and the second portion 504 represents a second image 512 of a second plane. The first plane and the second plane are disposed at different orientations. The first portion 502 includes a first icon 506 and the second portion 504 includes a second icon 508. The first icon 506 and the second icon 508 may be similar in form and function to the first icon 402 and the second icon 404 shown in FIG. 4A in accordance with an embodiment. The first image 510 and the second image 512 both show an anatomical object-of-interest 514. A line-of-intersection 516 is visible on both the first image 510 and the second image 512. According to an embodiment, the line-of-intersection 516 may be part of the user interface. For example, the user may adjust the position of the line-of-intersection 516 on either the first image 510 or the second image 512 so that the line of intersection is positioned on the relevant anatomy, such as the object-of-interest 512. For instance, the user may reposition the line-of-intersection 516, such as by clicking on the line-of-intersection 516, dragging it with a mouse or trackball, and positioning it through the object-of-interest 514. The processor 116 may automatically adjust the orientation of the second plane so that the second plane passes through the object-of-interest 514 along the line of intersection. According to an embodiment, a user may use the line-of-intersection to fine-tune the planes displayed on the display device.

According to other embodiments, data for one or more additional planes may be acquired as part of the multi-plane data. For example, the multi-plane data may include data for a third plane in a second fixed relationship with the first plane and the second plane. The processor 116 would automatically adjust a third orientation of the third plane in order to maintain the second fixed relationship of the third plane with respect to the first plane in response to manually changing the orientation of the first plane through the user interface 115. Additionally, according to embodiments, the processor 116 may be configured to enable the user to independently adjust the orientation of any one of the planes. For example, the user may selectively choose to adjust the planes in lock-step, or the user may independently adjust the orientation of only one of the planes. The user may, for instance, adjust a rotation or tilt of only the first plane or only the second plane in accordance with an embodiment.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:
1. A method of ultrasound imaging comprising:
   independently adjusting a first plane to a first orientation with respect to a second plane and a transducer array, where the second plane is disposed at a different orientation than the first plane with respect to the transducer array, wherein the second plane is in a fixed relationship with the first plane after independently adjusting the first plane to the first orientation;
   acquiring multi-plane data with the transducer array after independently adjusting the first plane to the first orientation, the multi-plane data including the first plane and the second plane;

displaying a first image of the first plane and a second image of the second plane, where the first image is an image of the first plane acquired as part of the multi-plane data and the second image is an image of the second plane acquired as part of the multi-plane data;

adjusting the first orientation of the first plane with respect to the transducer array with a user interface;

automatically adjusting the second orientation of the second plane with respect to the transducer array to maintain the fixed relationship between the second plane and the first plane after said adjusting the first orientation of the first plane;

acquiring additional multi-plane data of the first plane and the second plane after automatically adjusting the second orientation of the second plane with respect to the transducer array; and displaying a first updated image of the first plane and a second updated image of the second plane based on the additional multi-plane data, wherein the first updated image is of the first plane that was acquired as part of the additional multi-plane data, after said adjusting the first orientation with respect to the transducer array, and wherein the second updated image is of the second plane that was acquired as part of the additional multi-plane data after said automatically adjusting the second orientation with respect to the transducer array.

2. The method of claim 1, wherein said adjusting the first orientation of the first plane occurs during the process of said acquiring the multi-plane data.

3. The method of claim 2, wherein said automatically adjusting the second orientation of the second plane occurs during the process of acquiring the multi-plane data.

4. The method of claim 1, wherein said automatically adjusting the second orientation of the second plane, and said displaying the first updated image and the second updated image all occur in real-time in response to said adjusting the first orientation of the first plane.

5. The method of claim 1, further comprising displaying a third image of a third plane at substantially the same time as said displaying the first image and the second image, wherein the third plane is in a second fixed relationship with respect to the first plane.

6. The method of claim 5, further comprising automatically adjusting a third orientation of the third plane with respect to the transducer array to maintain the second fixed relationship of the third plane with respect to the first plane after said adjusting the first orientation of the first plane.

7. The method of claim 6, further comprising automatically displaying a third image of the third plane after said automatically adjusting the third orientation of the third plane.

8. The method of claim 1, wherein said adjusting a first orientation of the first plane comprises adjusting at least one of a tilt and a rotation of the first plane.

9. An ultrasound imaging system comprising:
a probe including a transducer array;
a display device;
a user interface; and
a processor in electronic communication with the probe, the display device, and the user interface wherein the processor is configured to:
enable a user to independently adjust a first plane to a first orientation with respect to a second plane and the transducer array, where the second plane is disposed at a different orientation than the first plane with respect to the transducer array, wherein the second plane is in a fixed relationship with the first plane after independently adjusting the first plane to the first orientation;

control the probe to acquire multi-plane data with the transducer array after independently adjusting the first plane, the multi-plane data including the first plane disposed at the first orientation and the second plane disposed at the second orientation;

display a first image of the first plane and a second image of the second plane on the display device while acquiring the multi-plane data, where the first image is an image of the first plane acquired as part of the multi-plane data and the second image is an image of the second plane acquired as part of the multi-plane data;

enable a user to adjust the first orientation of the first plane with respect to the transducer array with the user interface while acquiring the multi-plane data;

automatically adjust a second orientation of the second plane with respect to the transducer array to maintain the fixed relationship between the first plane and the second plane after adjusting the first orientation of the first plane; and control the probe to acquire additional multi-plane data after automatically adjusting the second orientation of the second plane with respect to the transducer array.

10. The ultrasound imaging system of claim 9, wherein the processor is further configured to display a first updated image of the first plane and a second updated image of the second plane, based on the additional multi-plane data, on the display device after automatically adjusting the second orientation of the second plane, where the first updated image is of the first plane acquired as part of the additional multi-plane data and where the second updated image is of the second plane acquired as part of the additional multi-plane data.

11. The ultrasound imaging system of claim 9, wherein the processor is further configured to enable the user to independently adjust a rotation of either the first plane or the second plane with respect to the transducer array with the user interface.

12. The ultrasound imaging system of claim 9, wherein the processor is further configured to enable the user to independently adjust a tilt of either the first plane or the second plane with respect to the transducer array with the user interface.

13. The ultrasound imaging system of claim 9, wherein the processor is further configured to enable a user to independently adjust both a tilt and a rotation of either the first plane or the second plane with respect to the transducer array with the user interface.

14. The ultrasound imaging system of claim 9, wherein the user interface comprises a rotary configured to adjust at least one of a tilt and a rotation of either the first plane or the second plane with respect to the transducer array.

15. The ultrasound imaging system of claim 9, wherein the user interface comprises a trackball configured to adjust at least one of a tilt and a rotation of either the first plane or the second plane with respect to the transducer array.

16. The ultrasound imaging system of claim 9, wherein the user interface comprises a graphical user interface configured to adjust at least one of a tilt and a rotation of either the first plane or the second plane with respect to the transducer array.

17. An ultrasound imaging system comprising:
a probe including a transducer array;

a display device;
a user interface; and
a processor in electronic communication with the probe, the display device, and the user interface wherein the processor is configured to:
  enable a user to independently adjust a first plane to a first orientation with respect to a second plane and the transducer array, where the second plane is disposed at a different orientation than the first plane with respect to the transducer array;
  control the probe to acquire data of the first plane and the second plane with the transducer array, where the second plane is disposed at a different orientation than the first plane with respect to the transducer array;
  display a first image of the first plane and a second image of the second plane based on the data, where the first image is an image of the first plane that was acquired and the second image is an image of the second plane that was acquired;
  adjust a first orientation of the first plane with respect to the transducer array and a second orientation of the second plane with respect to the transducer array in lock-step in response to a single control input through the user interface; and control the probe to acquire additional data of the first plane and additional data of the second plane after adjusting the first orientation of the first plane with respect to the transducer array and the second orientation of the second plane with respect to the transducer array.

18. The ultrasound imaging system of claim 17, wherein the processor is further configured to display a first updated image of the first plane based on the additional data of the first plane and a second updated image of the second plane based on the additional data of the second plane after adjusting the first orientation and the second orientation with respect to the transducer array, where the first updated image is of the first plane acquired as part of the additional multi-plane data and where the second updated image is of the second plane acquired as part of the additional multi-plane data.

19. The ultrasound imaging system of claim 17, wherein the probe is a 2D matrix array probe.

20. The ultrasound imaging system of claim 17, wherein the data comprises multi-plane data.

* * * * *